US008635282B2

(12) United States Patent
Berisford et al.

(10) Patent No.: US 8,635,282 B2
(45) Date of Patent: Jan. 21, 2014

(54) COMPUTER—AUTOMATED SYSTEM AND METHOD OF ASSESSING THE ORIENTATION, AWARENESS AND RESPONSES OF A PERSON WITH REDUCED CAPACITY

(75) Inventors: Kimberley Price Berisford, Raleigh, NC (US); Audrey Elizabeth Berisford, Raleigh, NC (US); Carl Henry Krienen, Jr., Raleigh, NC (US); Arthur Brown Bradsher, Durham, NC (US); Christopher Michael Bradsher, Durham, NC (US)

(73) Assignee: Kimberco, Inc., Raleigh, NC (US)

( * ) Notice: Subject to any disclaimer, the term of this patent is extended or adjusted under 35 U.S.C. 154(b) by 42 days.

(21) Appl. No.: 13/103,462

(22) Filed: May 9, 2011

(65) Prior Publication Data

US 2011/0276644 A1   Nov. 10, 2011

Related U.S. Application Data

(63) Continuation of application No. 12/494,005, filed on Jun. 29, 2009, now Pat. No. 7,966,378, which is a continuation of application No. 10/910,569, filed on Aug. 4, 2004, now Pat. No. 7,562,121.

(51) Int. Cl.
*G06F 15/16* (2006.01)
*G06Q 10/00* (2012.01)
*G06Q 50/00* (2012.01)

(52) U.S. Cl.
USPC ............ 709/205; 709/201; 709/203; 340/6.1; 340/7.2; 340/7.28; 705/2

(58) Field of Classification Search
USPC .................................. 709/201–206; 705/2, 3
See application file for complete search history.

(56) References Cited

U.S. PATENT DOCUMENTS

| 4,524,243 | A | 6/1985 | Shapiro |
| 5,441,047 | A | 8/1995 | David et al. |
| 5,544,649 | A | 8/1996 | David et al. |
| 5,769,269 | A | 6/1998 | Peters |
| 5,802,494 | A | 9/1998 | Kuno |
| 5,905,436 | A | 5/1999 | Dwight et al. |
| 6,002,918 | A | 12/1999 | Heiman et al. |
| 6,002,994 | A | 12/1999 | Lane et al. |

(Continued)

FOREIGN PATENT DOCUMENTS

| WO | WO 02/075687 | 9/2002 |
| WO | WO 03/102866 | 12/2003 |

*Primary Examiner* — Tae Kim
(74) *Attorney, Agent, or Firm* — Oblon, Spivak, McClelland, Maier & Neustadt, L.L.P.

(57) ABSTRACT

A system and method for scheduling, and reminding people receiving care (PRC) about upcoming events uses a remote computer-based interface that allows a Caregiver at a remote location to schedule the events for the PRC. The PRC has in their residence (or other location) a device that prompts the PRC, by an audio and/or video prompt, so as to "nudge" the PRC, asking whether they intend to participate in a pre-scheduled event. A man-machine interface, such as a two input keypad containing one button labeled "yes" and another button labeled "no", the remote Caregiver is able to monitor the responses of the electronic "nudges" offered by the system to the PRC. In turn, the device used by the remote Caregiver accumulates the responses and creates a history of the level of activity the person has indicated in which they wish to participate.

2 Claims, 11 Drawing Sheets

(56) References Cited

U.S. PATENT DOCUMENTS

| | | | |
|---|---|---|---|
| 6,049,281 A | 4/2000 | Osterweil | |
| 6,198,695 B1 | 3/2001 | Kirton et al. | |
| 6,307,481 B1 | 10/2001 | Lehrman et al. | |
| 6,445,298 B1 | 9/2002 | Shepher | |
| 6,497,367 B2 | 12/2002 | Conzola et al. | |
| 6,501,386 B2 | 12/2002 | Lehrman et al. | |
| 6,524,239 B1 | 2/2003 | Reed et al. | |
| 6,611,206 B2 | 8/2003 | Milanski et al. | |
| 6,614,348 B2 | 9/2003 | Ciccolo et al. | |
| 6,661,347 B2 | 12/2003 | Lehrman et al. | |
| 6,696,957 B2 | 2/2004 | Shepher | |
| 6,703,939 B2 | 3/2004 | Lehrman et al. | |
| 2001/0000431 A1 | 4/2001 | Lehrman et al. | |
| 2001/0016845 A1 | 8/2001 | Tribbensee | |
| 2001/0026223 A1 | 10/2001 | Menard et al. | |
| 2001/0048368 A1 | 12/2001 | Lehrman et al. | |
| 2002/0016729 A1* | 2/2002 | Breitenbach et al. | 705/9 |
| 2002/0118121 A1 | 8/2002 | Lehrman et al. | |
| 2002/0135484 A1 | 9/2002 | Ciccolo et al. | |
| 2002/0171551 A1 | 11/2002 | Eshelman et al. | |
| 2003/0058111 A1 | 3/2003 | Lee et al. | |
| 2003/0227386 A1* | 12/2003 | Pulkkinen et al. | 340/573.1 |
| 2003/0229471 A1 | 12/2003 | Guralnik et al. | |
| 2004/0019603 A1* | 1/2004 | Haigh et al. | 707/102 |
| 2004/0019654 A1* | 1/2004 | Powers et al. | 709/217 |
| 2004/0030531 A1 | 2/2004 | Miller et al. | |
| 2004/0147817 A1* | 7/2004 | Dewing et al. | 600/300 |
| 2005/0131736 A1* | 6/2005 | Nelson et al. | 705/2 |
| 2005/0240571 A1* | 10/2005 | Haigh et al. | 707/3 |

* cited by examiner

Figure 4 – Entering A Scheduled Activity

COMPUTER—AUTOMATED SYSTEM AND METHOD OF ASSESSING THE ORIENTATION, AWARENESS AND RESPONSES OF A PERSON WITH REDUCED CAPACITY

CROSS REFERENCE TO RELATED APPLICATIONS

This application is a Continuation of and is based upon and claims the benefit of priority under 35 U.S.C. §120 for U.S. Ser. No. 12/494,005, filed Jun. 29, 2009, which is a Continuation of U.S. Ser. No. 10/910,569, filed Aug. 4, 2004 (now U.S. Pat. No. 7,562,121, issued Jul. 14, 2009), the entire contents of each which are incorporated herein by reference.

BACKGROUND OF THE INVENTION

1. Field of the Invention

The present invention relates to computer-automated interactive systems and methods of assessing the orientation, awareness and responses of a person with reduced capacity (hereinafter "PRC"). More particularly, the system and method is directed to addressing scheduling activities and specialized instructions for the PRC, monitoring their interactive responses to invitations to participate in the activities, and subsequently, determining whether their responses are corroborated by the actual detected activities of the PRC. The present invention further provides a computer-automated system and method of performing automated actions in accord with the responses and actual detected activities.

2. Discussion of the Background Art

Though the present invention may be applied to the benefit of any PRC, for ease of understanding, some of its applications are hereinafter explained with respect to elderly persons. Moreover, a PRC should not be construed narrowly and includes anyone (blind, aged, hearing impaired, inexperienced younger people, non-native English speaking people, crippled, mentally challenged, etc.) who would benefit from an interactive system and method for providing reminders. In the special case where the PRC is an elderly person, because the elderly are more apt to incur a wide range of reduced capacities, such as cognitive, sensory, physical, and emotional capacity, they provide an excellent context within which to explain the present invention.

The United State's population of elderly is expected to double to 70 million by 2030. Much of that rise is due to the 76 million baby-boomers that will begin turning 65 years-of-age in 2011. This shift in demographics in the Untied States (for example) will give rise to very serious emotional and financial stress to a greater percentage of people who are the younger members, responsible for caring for their more elderly relatives. The cost of care for elderly people can be prohibitive, even for middle-class wage earners. An important aspect of a well-balanced financial plan for a modern family is to encourage all family members to take care of themselves and be self-sufficient for as long as possible so as to avoid being a drain on the financial resources of the rest of the family, and/or having to apply for government assistance. In addition to providing an enormous market for technology, the elderly (and of course most PRCs, and their families) stand to greatly benefit from technological advances for at least the reasons stated below.

Two areas in which the elderly are often in greater need are activity and supervision. Regarding the former, the elderly are more susceptible to inactivity caused by general depression (e.g., loneliness and malaise), physical discomfort (e.g., arthritis and fatigue), and lack of opportunities (e.g., lack of transportation or forgetfulness of upcoming events). The later cause of inactivity frequently results from a Caregiver's failure to apprise an elderly person of available activities or failure to realize that activities are currently unavailable to that person. Regardless of the reason, the present inventors recognize there is a need to notify, or simply remind, the elderly of available activities and to monitor that they are generally participating in the same.

Furthermore, the elderly are also more susceptible to severe and sudden declines in orientation, awareness and responses, such as being due to severe depression and its symptoms (e.g., failure to eat); and severe physical ailment (e.g., strokes and heart attacks). Unlike the above-noted problems, which should not be overshadowed, severe depression and physical ailment must be immediately addressed to prevent permanent or persistent disability or death. Accordingly, there is a need to immediately notify a Caregiver of inactivity, suggesting such depression or physical ailment.

U.S. Pat. No. 6,611,206, issued to Eshelman et al., is an example of a conventional technique for monitoring independent persons requiring occasional assistance. The system relies on the presence of a large number of different types of sensors (including video and audio), coupled with artificial intelligence programs, to monitor the activities of a person needing occasional assistance. In the several examples described, such as Example 1, cameras are aimed at a child sleeping in a crib, and a microphone is placed in a position to pick up sounds. A controller is programmed to recognize the normal look of the baby's face and recognize the sound of crying and produce a signal that crying occurs. The controller is also configured to analyze the facial expressions of the infant so as to determine whether the infant is crying, playing, in distress, or expressing other moods that may be remotely observed by a caretaker. In a second example, an elderly person lives alone and is observable via multiple video cameras and audio microphones located throughout the house. These sensors are able to recognize the activity level of the person and when used with a controller, are able to assess their particular mood. For example, using artificial intelligence, the system may be trained to recognize frustration in detecting the elderly person's utterance of periodic clipped speech using words indicative of a negative mood.

The present inventors have recognized that a limitation with conventional approaches such as that described in U.S. Pat. No. 6,611,206 is that elderly people merely need occasional assistance, and have no interest in losing their dignity by having all of their activities monitored by "Big Brother". A common limitation with elderly people is forgetfulness. A system such as that described in U.S. Pat. No. 6,611,206 would be overly intrusive simply for the purpose of reminding a person about a particular planned activity.

There are conventional scheduling software applications, such as MICROSOFT OUTLOOK, that permit users to schedule an event, to generate messages reminding themselves or others that the event is impending, to generate invitations requesting a response as to whether the invitee will attend, and to monitor the responses of the invitees. With the advent of digital networks, e.g., the Internet, scheduling applications have further permitted users to perform these functions via remote devices; and to remotely receive and respond to the reminder messages and/or invitations. Thus, presumably, some Caregivers might try to use a conventional scheduling application to schedule an upcoming event, notify an elderly person of the event, and determine whether that person intends to attend the event (e.g., via R.S.V.P.). It bears mention that the success of such an endeavor may indicate the elderly person is not a PRC in need of such services.

FIG. 9 is a flow chart showing a conventional process for monitoring the activities of a PRC. The process begins in step S101, where specific sensor tags are attached to objects whose movement indicates daily activities of the PRC. For example, the sensor tags would include a toothbrush, coffee mug, and other objects that typically would be used by a PRC who is functioning self-sufficiently with regard to those particular objects. Subsequently the process proceeds to step S102, where the sensor tags are also attached to particular devices associated with taking the PRC's medications. As an example, the sensors may be attached to the medicine cabinet doors, pill boxes, or pill dispensers. Subsequently the process proceeds to attaching sensor tags to the elderly person's body, perhaps in the form of a bracelet, and attaching smart sensors to where the measurement of the respective sensors indicate specific psychological conditions. As one example, the sensors may be placed in the person's shoes in order to indicate the regular/irregular gait of that particular person.

The process then proceeds to step S105 where the movement of the respective sensors are analyzed to determine the level of activity of that person. The process then proceeds to assess the data received by the sensors arranged in step S104 to determine the specific psychological condition of the PRC. Based on the data received in the above steps, the process proceeds to step S107, where the Caregiver is notified of inadequate or irregular activity where indicated by the above process steps.

Further, many operating systems, add-on software applications, and specialty devices make the user interfaces of such scheduling applications more accessible to PRCs. As a result, presumably, some computer-literate PRCs might use scheduling applications without the on-site assistance of another person, regardless of the nature of their impediment.

Further, sophisticated systems are currently available that monitor the activity of a PRC at arms length. For instance, sensors are currently employed to detect whether a PRC has awakened and used a bathroom facility. Intel Corporation is reportedly testing a system of sensors and devices for the elderly that issues medication reminders and determines an elderly person's level of activity. General Electric is similarly reported to be testing a system that detects abnormal behavior of an elderly person and accordingly transmits an automated alert of that behavior to a Caregiver.

FIG. 11 is a block diagram of a web-based system for sending photographs to be displayed on a photoviewer 1100 for people who are not computer literate. CEIVA (see www.ceiva.com) sells a receiver 1100 that looks like a picture frame, but is able to display digital photographs sent to if from a server 1105. Moreover, a family member uses their computer 1103 to upload their photos to the server 1105 via a network (such as the Internet and/or public switched telephone network). The receiver 1100 at a predetermined time (e.g., 2 AM) dials into the server 1105 and downloads photos to the receiver, which are then displayed as pictures in a photo frame. This system is quite convenient for people who are not computer literate, such as many PRCs, because once the system is set up, they need to do nothing, yet they are able to view updated photos sent from family members. Family members upload the photos by logging on to the www.CEIVA.com website and responding to the prompts on the web page to upload photos to the server 1105.

As the inventors of the present invention have recognized, none of those products provide a computer-automated system and method of assessing the orientation, awareness, and responses of PRCs by remotely scheduling activities for them and then monitoring their interaction with the system, such as "yes", "no" responses to invitations to participate in those scheduled activities. It follows that none of the products compare a PRC's responses to such invitations against a sensed activity of the PRC; and none of the products permit a remote programming of automated actions that are performed in accord with the PRC's responses to such invitations and/or in accord with whether the PRC's responses and sensed activities are congruous with one another.

SUMMARY OF THE INVENTION

In view of at least the above-noted problems and deficiencies of the background art, an object of the present invention is to provide a remote scheduling and monitoring system that addresses the above-identified and other limitations of conventional systems and methods. The system and method of the present invention uses a remote computer-based interface that allows a Caregiver at a remote location to schedule events for the PRC. Alternatively, the scheduling may be done on the device that the PRC will actually use. In either case, the PRC has in their residence (or other location) a device that either audio or video prompts the PRC to "nudge" them, asking whether they intend to participate in a pre-scheduled event. Using a simple man-machine interface, such as a two input keypad containing one button labeled "yes" and another button labeled "no", the remote Caregiver is able to monitor the responses of the electronic "nudges" offered by the system to the PRC. In turn, the device used by the remote Caregiver is able to accumulate the responses and create a history of the level of activity the person has indicated they wish to participate in. This data may then be corroborated with reports from third parties (and/or sensors) indicating whether the third party has actually participated in those events.

BRIEF DESCRIPTION OF THE DRAWINGS

A more complete appreciation of the present invention and many of the attendant advantages thereof will be readily obtained as the same becomes better understood by reference to the following detailed descriptions of the present invention, and when considered in connection with the accompanying drawings, wherein.

DETAILED DESCRIPTION OF THE INVENTION

Figure 1:
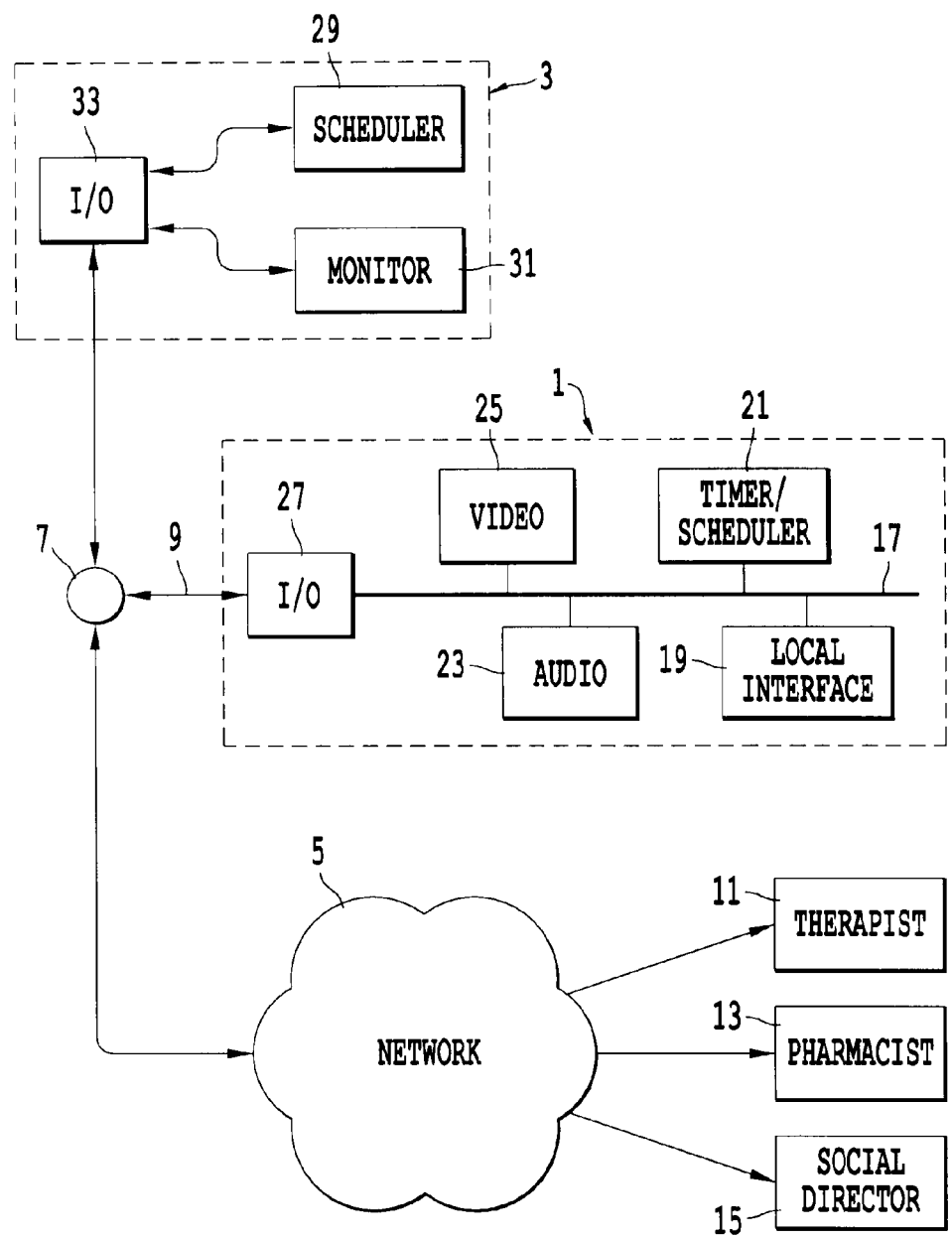
FIG. 1 is a system block diagram of an embodiment of the present invention.

Referring now to the drawings, wherein like reference numerals designate identical or corresponding parts or steps, FIG. 1 illustrates a system block diagram of a PRC scheduling and interface system according to the present invention. A local interaction device 1, commonly placed in the residence of the PRC, is connected by way of a communication link 9 by way of a router or switch 7 (optional) as part of a network 5 to a remote interface 3. Moreover, this connection between the local interaction device 1 and the remote interface 3 may be performed by any one of a number of ways, including direct physical connection (e.g. Ethernet, dialup network, Internet connection, wireless link, or hybrid combinations). The network 5 also connects to various third parties, such as equipment (like the remote interface 3) used by a therapist 11, a pharmacist 13, and social director 15, as will be discussed.

The local interaction device 1 is the device located near the PRC and is used by the PRC to respond to notifications or alarms scheduled by a Caregiver. As an example, the remote interface 3 is used by a Caregiver to set a particular event for announcement to the PRC by way of the local interface device 1. This announcement may be, as an example, a video announcement displayed on video device 25 (e.g. a TV, a computer monitor, or a local display on the local interface device). The alarm may also be an audible alarm or a combination of an audible alarm and a video announcement, where the audible alarm is produced by an audio interface 23 that includes a speaker(s). A timer/scheduler 21 recognizes when the time has arrived to dispatch a command for making the scheduled announcement to the PRC.

In response to the command, the scheduler 21 sends a signal over bus 17 to the video device 25 and/or audio device 23 to announce to the PRC that the event is coming soon, and inquires whether the PRC plans to attend. The PRC can then reset the alarm by interacting with the local interface 9, as will be discussed in more detail with regard to FIG. 3. Typically, the local interface 19 provides two responses (affirmative, or negative) by the PRC that will be recognized by the local interaction device 1. One response is made by the PRC pressing a button labeled "yes", indicating that the PRC would like to participate in the event. The local interface 19 also includes a second button labeled "no", which if pressed by the PRC would indicate that the PRC does not have an intention to attend the event.

Figure 3:
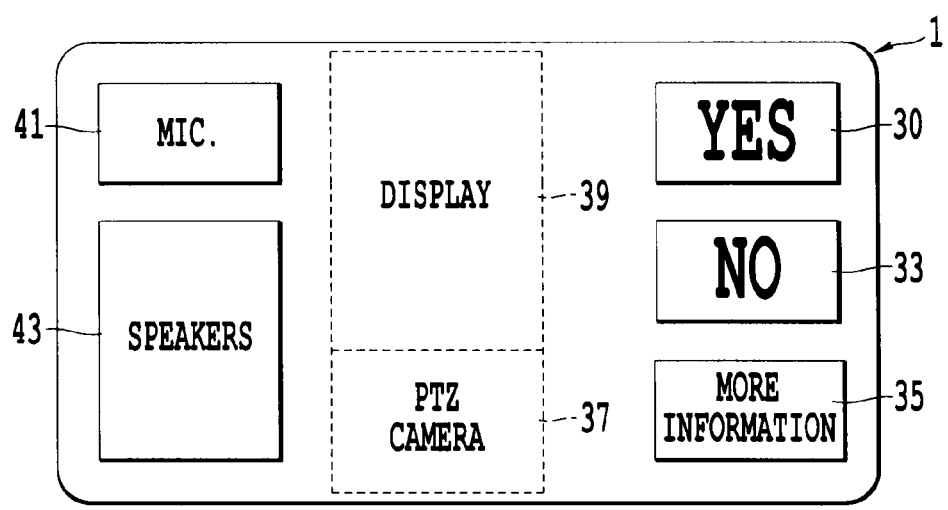
FIG. 3 is a block diagram of a local interaction device used by the PRC.

As will be appreciated from the discussion with regard to FIG. 3, the local interface 19 need not be limited to the use of buttons, but may also use other man-machine interfaces configured to detect the PRC's preference. As an example, the local interaction device 1 may receive an audio indication from the PRC (such as a spoken work "yes"), indicating the PRC's intentions with regard to the scheduled event. Likewise, the video device 25 may take a short video clip of the individual when the individual steps within a certain proximity (e.g. 10 feet) of the device, as sensed by a motion detector or tactile sensor (neither is shown). The PRC may indicate his or her preference by either shaking his or her head, indicating "no", or nodding his or her head, indicating "yes". These physical actions are then recorded in a video clip (or file) that is saved to memory and subsequently transmitted to the remote interface 3 at a predetermined time (such as when requested by an operator of the remote interface 3). The video file (or more generally "interaction data") is then sent by way of an input/output (I/O) device 27 and the communication link 9 (perhaps including the network 5 and router 7) to the I/O device 33 in the remote interface 3. This video file is provided to the monitor device 31, which collects the data and compares the same against a prestored threshold.

As an example, when the PRC provides a tactile response by way of the local interface 19, indicating his or her preference. The monitor 31 ultimately receives the corresponding interaction data and stores the same for comparison against the predetermined threshold. In the case of the audio signal provided from the PRC, the monitor 31 uses a voice detector to determine whether the individual said yes or no (as an example) indicating his or her preference. Similarly, with the video signal is left by the PRC, the monitor 31 performs image recognition processing to determine whether the individual is shaking his or her head sideways (indicating a negative response), or nodding up and down (indicating an affirmative response). On the other hand, the system may also save the audio and video replies for audible and visual observation by the Caregiver.

In an alternative embodiment a separate monitor 31 is also included in the local interface device 1. This way, a person visiting the PRC may retrieve the data collected at the local interface device 1.

Regarding the scheduler 29 in the remote interface 3, the Caregiver uses the scheduler 29 to input (in text format as an example) a reminder for a certain activity for the PRC. The reminder may indicate, as an example, that there is a bridge game scheduled for a predetermined time during that day, and at predefined intervals (hourly intervals prior to the event) input from the scheduler 29 which is downloaded by way of the I/O 33 and communication link 9, and is stored in the timer/scheduler 21 of the local interaction device 1. In this way, the Caregiver may set in advance particular events for the PRC to be made aware of, and requiring that the PRC provide some interaction with the local interaction device 1, indicating his or her preference for attending the event or not. The scheduler 3 is implemented in software and provides a graphical user interface, prompting the user for data to be entered. A same scheduler 29 may be included in the local interaction device 1.

Similarly, aside from Caregivers, a therapist 11 may have a similar system to the remote interface 3 (perhaps without the monitor, but not necessarily) so that the therapist can schedule particular events and provide reminders to the PRC. For example, perhaps the therapist has arranged for a series of walks for the PRC during the day. The therapist can set the schedule for the PRC and provide reminders for the PRC to comply with the therapists' request. The therapist may then monitor the responses of the PRC to see if the PRC is properly adhering to the scheduled exercises.

Similarly, a pharmacist 13 (or even a physician, not shown) may use the remote interface 3 to input reminder data for the PRC to take certain medications at certain times during the day and request confirmation (or merely monitor the responses) that the PRC has actually taken the medication. Likewise, a social director 15 may schedule social activities for the PRC and request confirmation that the PRC intends to attend the scheduled events.

For the most part, the description of the present invention has been made in the context of the local interaction device generating a reminder prior to an even occurring. However, the present invention is also useful to generate reminders after an event has been detected. For example, when a signal is generated by a sensor (e.g., a magnetic reed switch) attached to a door, detecting that the door was opened, the signal is provided to the local interaction device 1 via the I/O 27. The signal triggers a reminder (audio, video or both) for the PRC to do something. Some memory-challenged people often forget where they have placed their purse, or their keys. In this situation, the Timer/Scheduler 21 is programmed to generate an audio announcement, reminding the PRC to place their purse or keys in a predetermined location, such as "put the keys in the bowl."

In this embodiment, MICROSOFT WINDOWS 2000 and MICROSOFT OUTLOOK may be installed in a typical fashion on the local interaction device 1. OUTLOOK's built-in calendar may be used as the engine managing the scheduling of activities, but OUTLOOK's user-interface is preferably replaced with a customized set of user screens programmed via a standard programming language (e.g., MICROSOFT VISUAL BASIC).

A system-level description of steps performed according to the present invention is discussed with reference to FIG. 2. The illustrated steps are subsequently discussed in greater detail with reference to the other figures. More particularly, steps S210, S220, S230, S240, S250, and S260 are further described with reference to later Figures.

Figure 2:
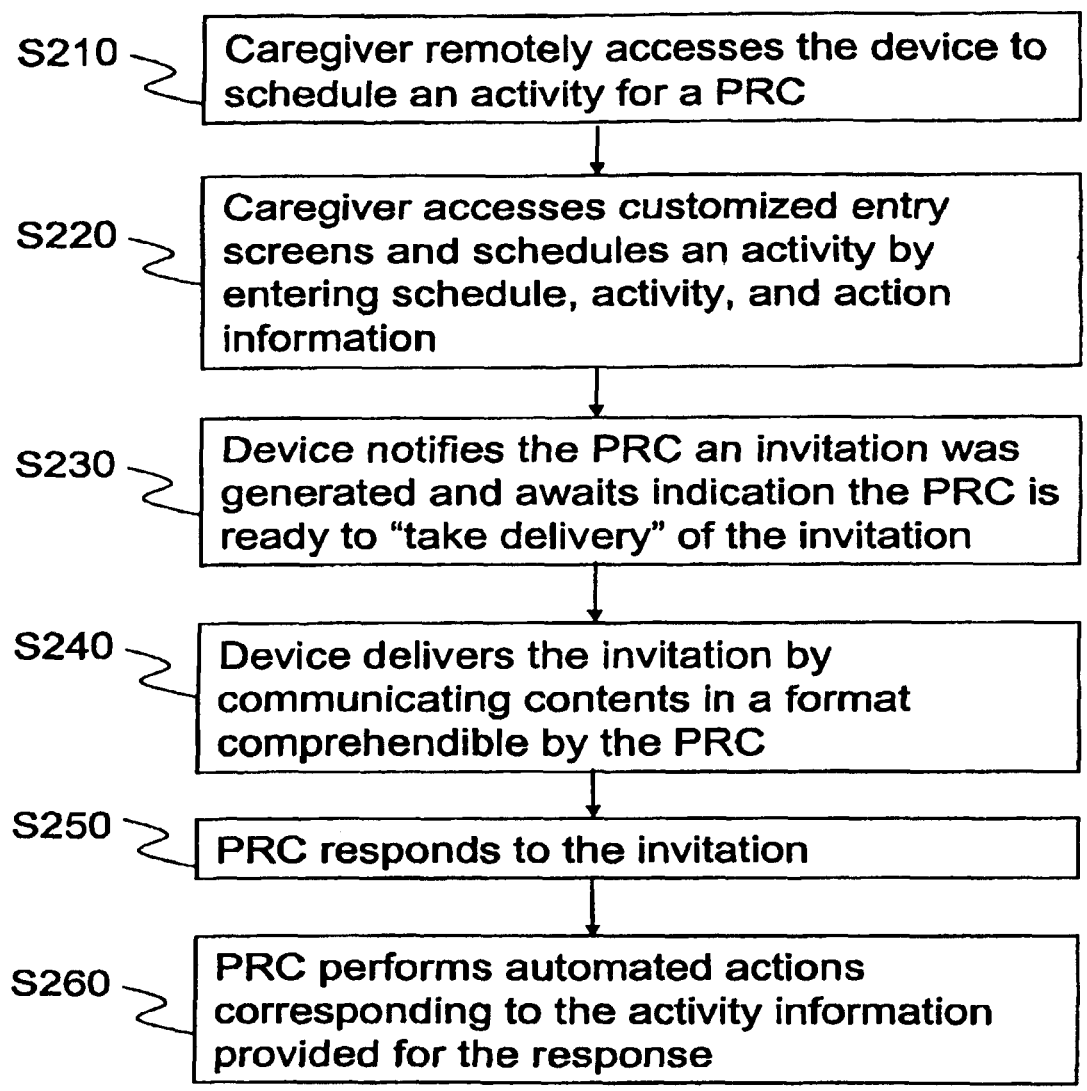
FIG. 2 is a process flow diagram showing a general overview of steps provided by an embodiment of the present invention.

FIG. 2 shows that the Caregiver first remotely accesses the local interaction device 1 (S210), using for example GOTO-MYPC software, to schedule an activity for the PRC (S220). Alternatively, the Caregiver may directly access the local interaction device 1 onsite by way of the timer/scheduler 21, or separate scheduler 29, if installed in the local interaction device 1. The Caregiver enters first, second, and third sets of information to schedule activity (S220), respectively. The first set may include schedule information such as the activity name, date, time, duration, location, and activity reoccurrence. The second set may include activity information such as the activity description, arranged transportation, attire, other indicating they will attend, and other information. The third set may include action information such as the automated actions corresponding to the PRC's response to a respective invitation (e.g., email daughter@work.com, if there is no response to the invitation repeated a predetermined number, such as 5 times).

An optional feature of the system is the inclusion of a graduated interaction mechanism included in the timer/scheduler 21 included as part of the local interaction device 1. The graduated interaction mechanism allows a computer savvy PRC to set his or her own scheduled reminders when at a highest grade-level of interaction, but later limits the amount of programmability by the PRC to a lowest grade-level when the PRC's abilities degrade. The number of gradations (e.g., grades 1 through 5) is not critical, as long as there is an association between grade level and degree of autonomy the PRC has over the scheduling and monitoring functions of the system. As an example, a newly retired or very moderately impaired individual who has computer skill and Internet capabilities might be highly involved in determining what activities to be involved in, and input such to the system. As the PRC's abilities (either mental or physical) decrease, the timer/scheduler 21 is adjusted (manually, or remotely by the caregiver or PRC) to become more restrictive (e.g., decrease from a grade level of 1 to 3, on a scale of 1 to 5, for example), to perhaps allow the PRC to provide yes/no responses, and schedule social activities, but not medicinal or therapeutic, as an example. Later, as the PRC's abilities degrade further, the grade of the timer/scheduler 21 is reduced to the lowest grade, 5, where the PRC is allowed only to enter "yes" or "no" responses.

After the activity is scheduled (S220), the local interaction device 1 notifies the PRC of a generated invitation (S230) by any number of measures (e.g., produces a particular sound, flashes the household lights, or transmits to a pager worn by the PRC), including simply displaying the invitation on the screen of the local interaction device 1. Upon determining that the PRC is ready for the invitation (an optional step, in which the PRC provides feedback that the PRC wants to receive the invitation), the device announces the invitation (S240) in a format tailored for comprehension by the PRC (e.g., displaying large font text and utilizing the aforementioned text-to-speech software, as well as the other notice functions discussed above).

The PRC may respond to the invitation (S250) by indicating "YES", "NO", or providing no response. In the present embodiment, the PRC will provide a tactile response "Yes" or "No" by activating the oversized buttons on the local interface 19. Alternatively, the PRC may also respond by requesting "MORE INFORMATION". In either matter, each response triggers the local interaction device 1 to perform an automated action (S260), which is tailored to the action information entered by the Caregiver in step S220 and based on the PRC's response, sensed activity, or both.

Figure 11:
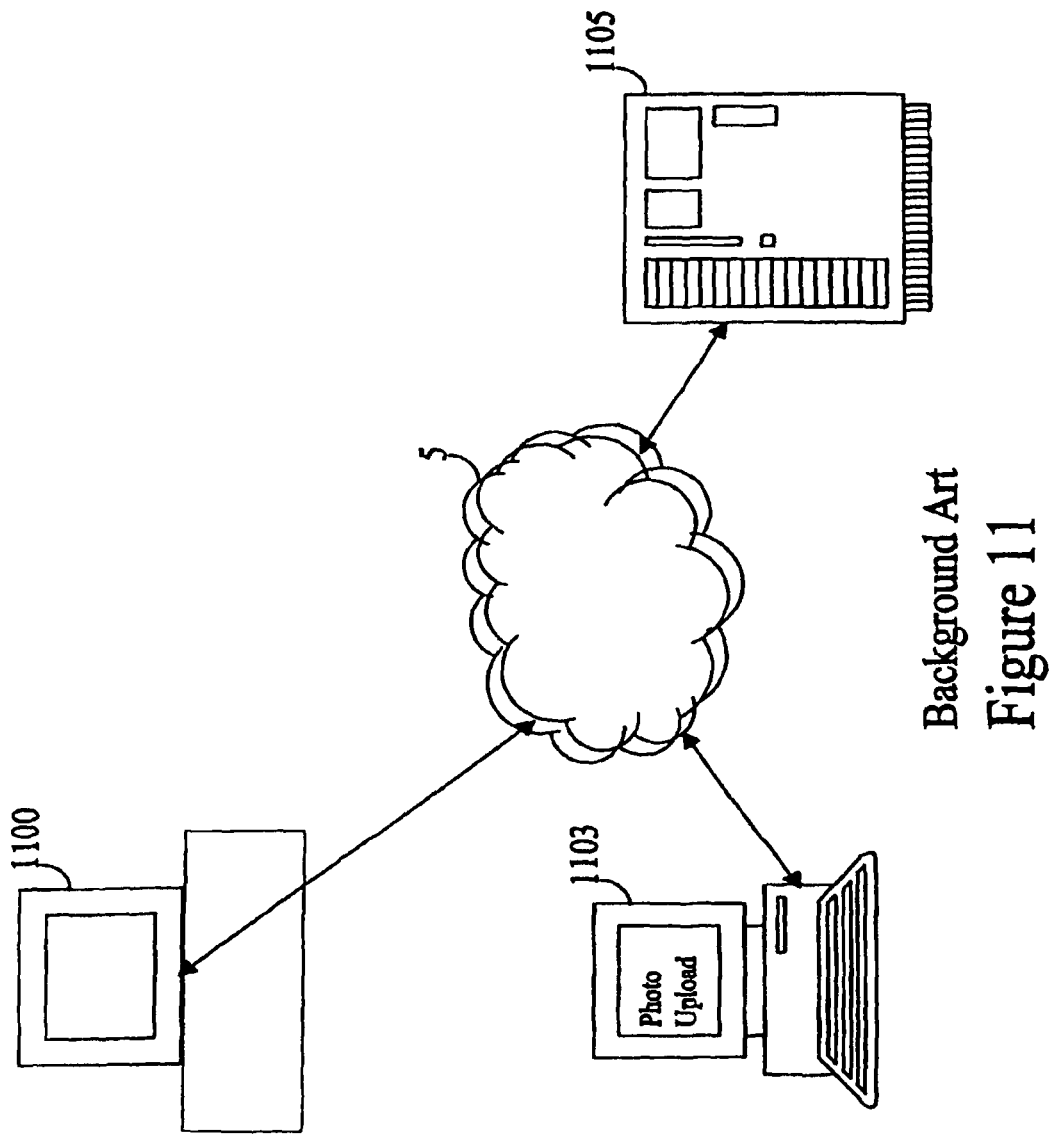
FIG. 11 is a block diagram of a conventional system for downloading photos to an individual for viewing on an electronic viewer, which is not a personal computer.

FIG. 3 is a block diagram of the local interaction device 1. The local interaction device 1 may be a standalone device, having a processor and I/O for connection over a network (such as a modified version of the electronic picture frame 1100 previously discussed with regard to FIG. 11). Alternatively, and as shown, is a peripheral device detachably attaches to a personal computer by way of a peripheral bus, such as a USB bus, FIREWIRE interface, or the like. The local interaction device 1 includes a microphone 41 (optional) for receiving audible input provided by the PRC. For example, the PRC may provide an audible response in reply to a scheduled event that is used to notify the PRC of the upcoming event. One or more speakers 43 are also included either embedded in the local interaction device 1 or attached thereto. The speakers provide audible announcements from the local interaction device 1 for listening by the PRC. The local interaction device includes an optional display 39 that can display text messages, or pictures, indicating the upcoming event. As an example, the picture may be a digital file (as will be discussed with regard to FIG. 8) that is downloaded from the remote interface 3 (FIG. 1). Moreover, the display 39 may be more suitable for some PRCs who would rather receive a visual display, rather than an audio alarm.

The local interaction device 1 optionally includes a pan, tilt, zoom camera 37 that may be connected to a motion detector. Moreover, when the PRC moves within a predetermined distance of the local interaction device 1, the PTZ camera 37 is actuated, and records the activities of that individual (nodding one's head or shaking one's head). The PTZ feature of the camera 37 may be used for automatic tracking of the PRC or remotely controlled (zoom, tilt or pan) by way of the remote interface 3.

The "yes" button 30 and "no" button 33 provide a tactile interface for the PRC to indicate his or her intent to reply to the subject of the alarm. For example, if an audible alarm announces a planned bridge game in one hour, the PRC if he or she chooses to go presses the "yes" button 30. The data would then be sent to the remote interface 3 (and also stored locally) for keeping track of the data. Optionally, a "more information" button 35 may be used to obtain any additional information available from the remote interface 3 or the local interaction device 1, should the "more information" button 35 be pressed by the PRC.

Although the tactile interface shown in FIG. 3 is in the form of buttons, other interfaces may be used as well, such as pressure sensors, capacitively coupled switches, or a touch screen interface.

The local interaction device 1 may also be portable and battery operated so as to be taken with the PRC to the particular activity. As an example, because the information is located in the local interaction device 1, and because the local interaction device 1 may be a self-contained portable unit (such included in or on a PDA, cell phone, hearing aide, watch, pendant, bi-focal frame, or even a larger device that is adapted to contain a two-way wireless, e.g., infrared or radio frequency communication capability) the schedule events may alert the PRC while the PRC is out of his or her residence. For example, if the PRC is participating in an activity, the PRC may need additional guidance regarding now to return home. For example, if a bus is scheduled to pick-up the PRC at a predetermined time from a museum, then this mobile version of the local interaction device 1 will sound an alarm alerting the PRC prior to the arrival of the bus. Also, if the PRC becomes apprehensive about how he or she will return to his or her residence, the PRC is able to view the activity on the local interaction device 1, informing the PRC about the issue that he or she is concerned about.

Figure 4:
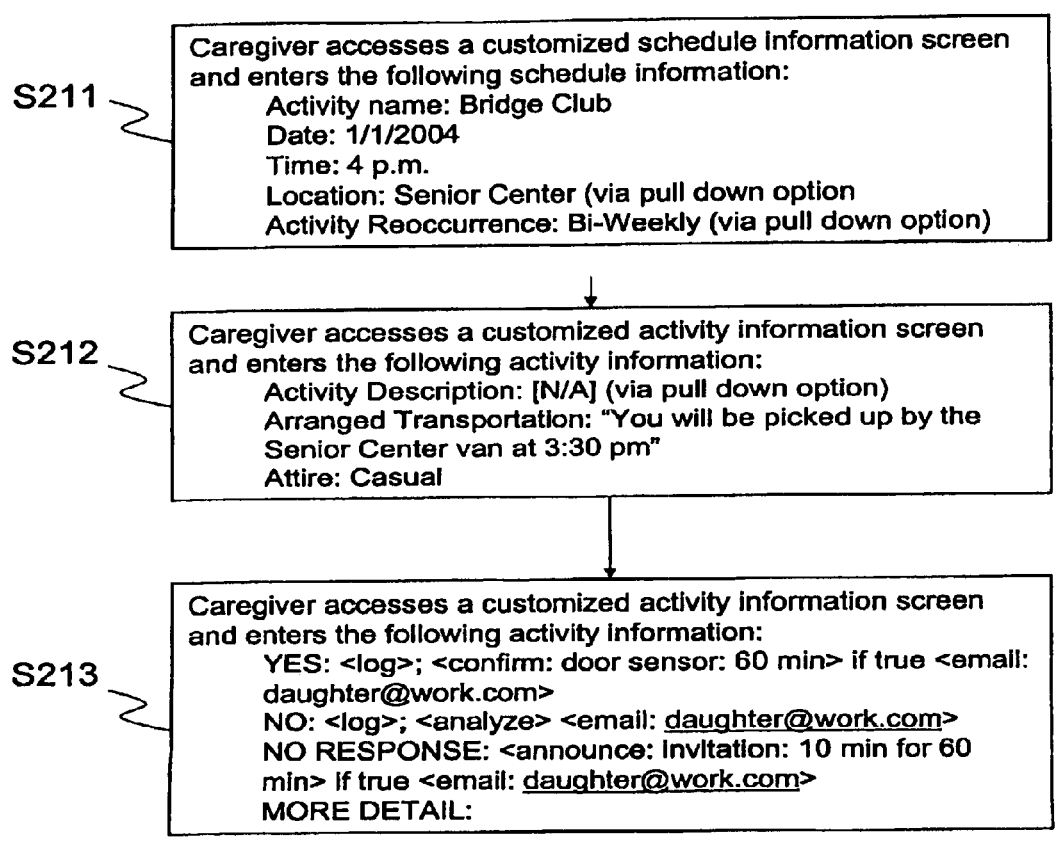
FIG. 4 is a flow diagram of a process for scheduling an activity for a PRC.

FIG. 4 is a block diagram showing an example of how to enter a scheduled activity for the PRC via the remote interface 3. As shown, the Caregiver first accesses a graphical scheduling information screen, and is prompted to enter schedule information which includes the activity name, day, time, location, and reoccurrences of the activity (S211). In this instance, the Caregiver has entered Bridge Club, Jan. 1, 2004, 4 p.m., Senior Center, and Bi-weekly, respectively, for the schedule information. Since "Senior Center" and "Bi-weekly" have been previously entered, those entries were entered via a pull down menu option.

Some of the schedule information entries are stored as text strings, e.g., "Bridge Club" is stored as a string corresponding to [activity name], to be later used when announcing the contents of the invitation; and some of the schedule information is stored as commands for automated actions of the device 1. For instance, the entry "bi-weekly" corresponding to [reoccurrences] prompts the device 1 to repeat the invitation (see below) every two weeks on date and time provided. Optionally, the Caregiver may elect to set the time(s) before the event the announcement is made, the duration of the announcement, and the number of times the announcement is made.

In step S212 the Caregiver is prompted to enter information describing some of the administrative aspects of the activity. For example, the transportation means for how the PRC will be taken and received, as well as the attire.

After entering the schedule information and activity information, the Caregiver accesses the customized action information screen, and enters a corresponding action (or no action) for each permitted response of the PRC (S213). In this instance, again, pull down options are available for frequently used entries. Two such entries are <log> and <analyze> which collectively prompt the device to log the response and determine (e.g., calculating) whether the PRC's recent level of inactivity has exceeded a prescribed level.

In this instance, the Caregiver has also entered <e-mail: van@seniorcenter.org> to instruct the device to send an e-mail to the senior center confirming the PRC will attend the Bridge Club meeting and need a ride thereto. In addition, the action entered for the "Yes" response also includes the command/s "<monitor: door sensor> (if true) <email: daughter@work.com>", which prompts the device to email the daughter if a particular door sensor is not activated in the next 60 min. Such notification would indicate that the door was not opened during the time period in which the PRC should left the home for the Bridge Club meeting.

Likewise, the therapist or social director who may be in charge of monitoring the activity that the PRC participates in, may input into their remote interface, an indication that the PRC has or has not attended. By this corroborating information, the Caregiver receives reliable information, verifying the PRC has in fact followed through on their expressed intention to participate in an activity.

Figure 5:
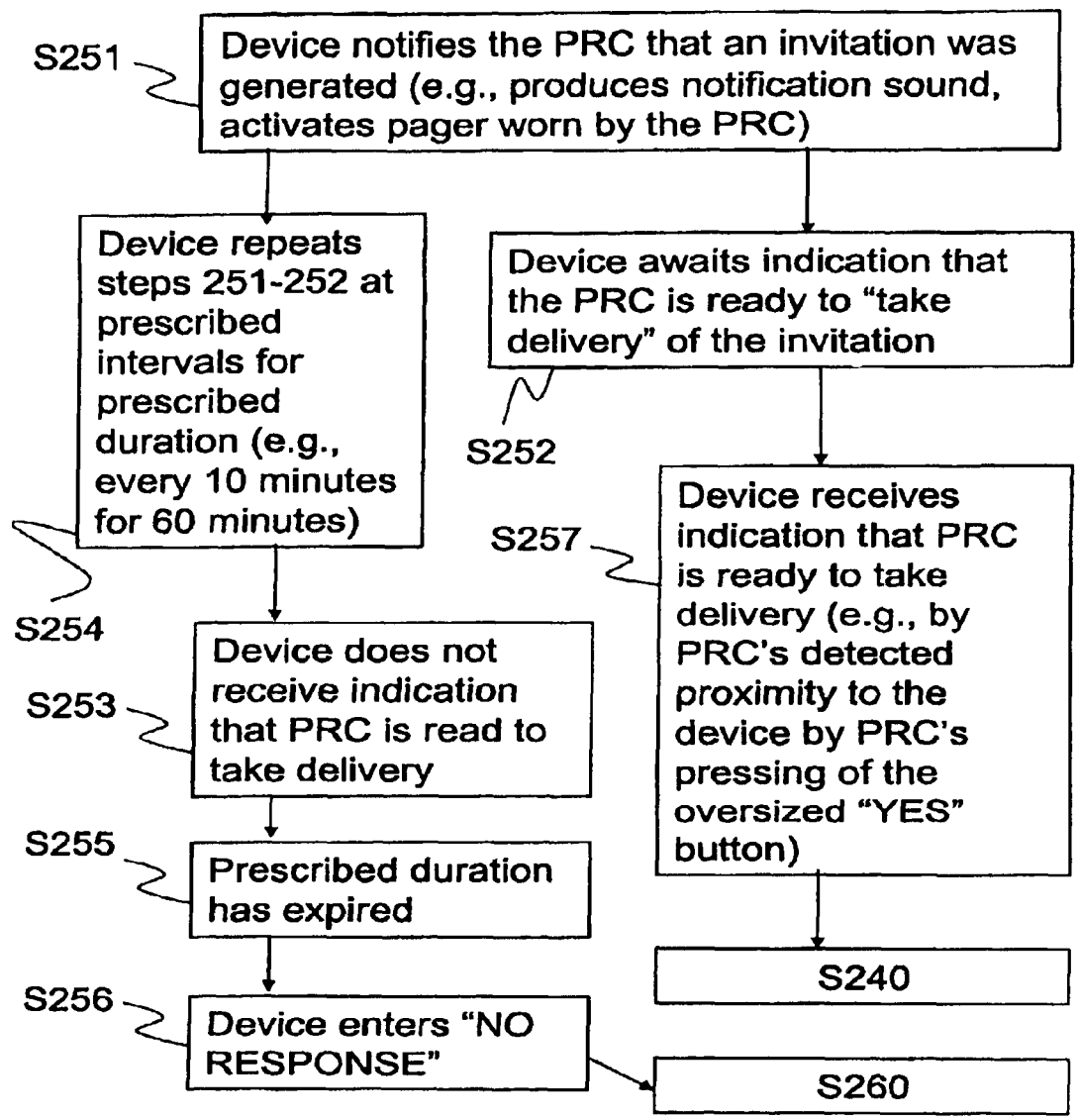
FIG. 5 is a flow diagram of a process for inviting the PRC to participate in a scheduled activity.

FIG. 5 is a more detailed description of the events that occur in step S250. In particular, in step S251, the local interaction device 1 notifies the PRC that an invitation was generated. Subsequently, the process includes two parallel series of steps. For the first series, in step S252 the device awaits an indication that the PRC is ready to take delivery of the invitation (optional). Subsequently, the process proceeds to step S257, where the device receives an indication that the PRC is ready to take delivery (for example by the PRC's detected proximity to the device or by the PRC's pressing of the oversized "YES" button). The process then proceeds to step S240 (discussed previously).

In the second series of steps, the device repeats steps S251 and 252 at prescribed intervals (programmable) for a predetermined duration (e.g., every 10 minutes for 60 minutes). The process then proceeds to step S253 where the device does not receive an indication that the PRC is ready to take the delivery. Then, in step S255 the prescribed duration period expires and the device determines that a "no response" was entered in step S256, prior to the process proceeding to step S260. In this way, the process provides a failsafe mechanism for providing a response to the device even if the PRC chooses not to interact with the local interaction device 1.

Figure 6:
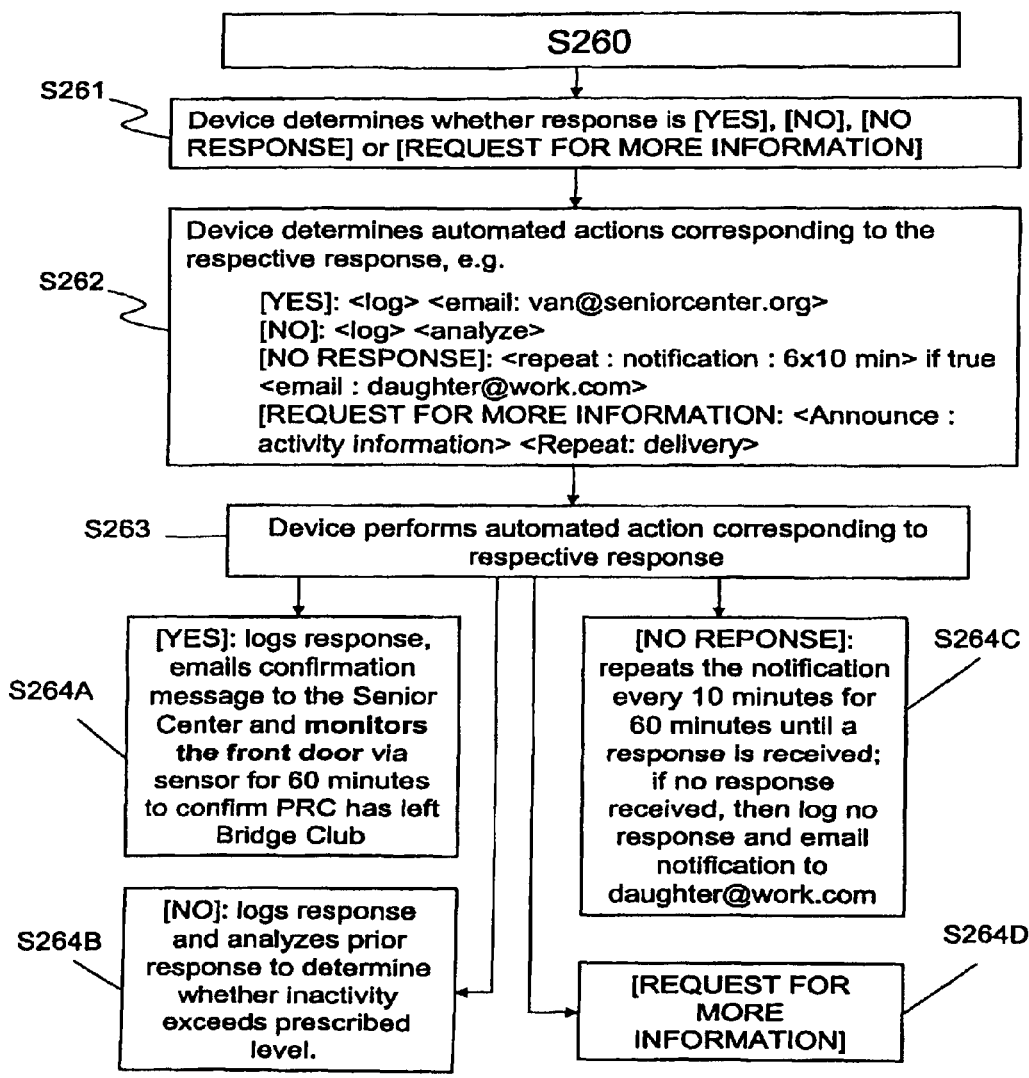
FIG. 6 is a flow diagram of a process for performing automated actions in accord with a response of the PRC.

FIG. 6 describes in more detail the substeps performed in step S260. In step S261, the device determines whether the PRC entered a tactile response of "YES", "NO", request for more information, or offered no response. Subsequently, the process proceeds to step S262, where the device determines automated actions to take that correspond to the received response. In this example, if the PRC enters "YES", then the device sends an e-mail (or other automated response, such as a voice mail indication) to the cooperating entities, in this case a van service operated at the senior center. If the response is "NO", then the data gets analyzed and compared to predetermined thresholds which will be discussed with regard to FIG. 7. If no response is received, then the process repeats the notification at 10 minute intervals (or other predetermined intervals) and if still no response is received after a predetermined number of intervals, then an automated message is sent to a primary Caregiver, in this case perhaps an e-mail to a daughter who is at her office during working hours. If the PRC requests additional information, then the device will provide a reiteration of the original announcement as well as a presentation of other information. In one example, this other information may contain an audio message from the Caregiver, informing the PRC why this particular activity may be important. For example, the Caregiver may include an audio message that says "Don't forget that it is Martha's birthday today. You can tell her this at the bingo game".

The process then proceeds to step S263 where the device performs an automated action corresponding to the respective response and then if the response is "YES', the device logs a response, e-mails the confirmation message and monitors the front door via the door sensor for the next 60 minutes to confirm that the PRC has in fact left for the bridge club. On the other hand, if the response is "NO", the device logs a response and analyzes the prior response to determine whether the inactivity exceeds a predetermined level (S264B). In no response is received then in step S264C the device repeats the invitation a predetermined number of times and then if necessary contacts the primary Caregiver. Likewise, if the PRC makes a request for more information than in step S264D, the information is provided as discussed above.

Figure 7:
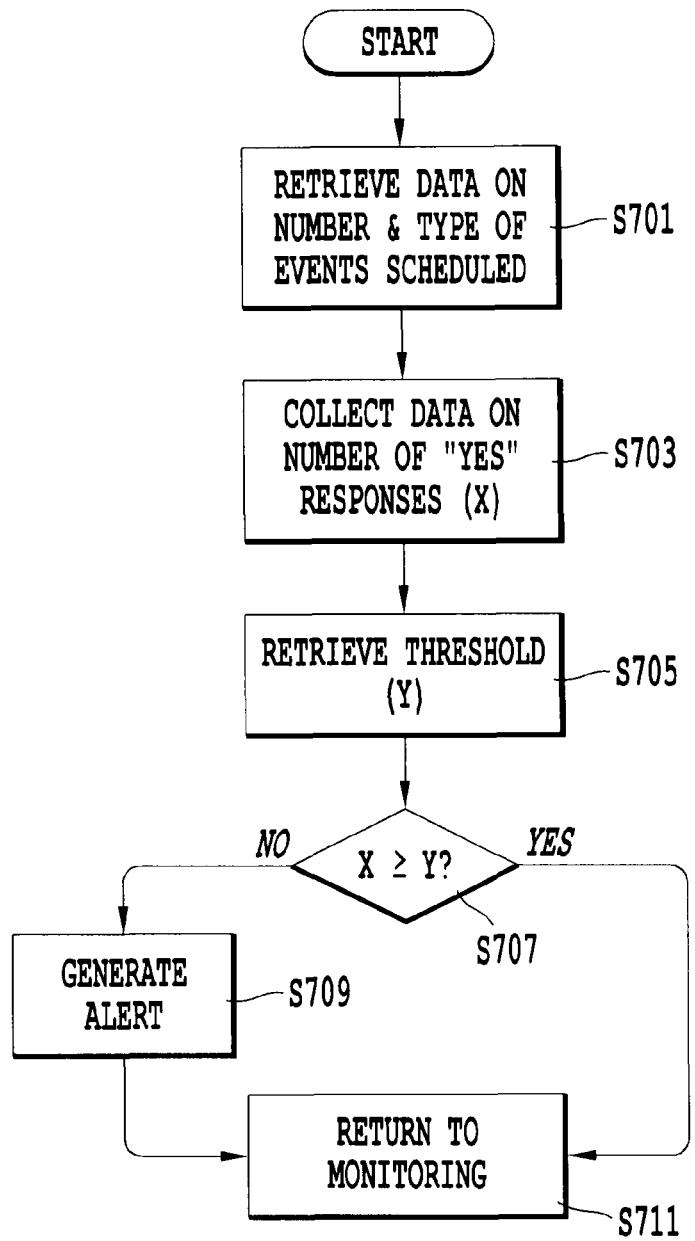
FIG. 7 is a flow diagram of a process for comparing data received from the local interaction device, and comparing the same against predetermined thresholds for determining a status of the PRC.

FIG. 7 is a flowchart showing how the data received from the local interaction device 1 is analyzed to determine the status of the PRC. The process begins in step S701, where the data is retrieved at the remote interface 3 (or alternatively at the local interaction device 1, or even at a physician or therapist's office, not shown in this figure). The data will include anywhere from one to a larger number of observed activities. Each activity is optionally given a predetermined weight of importance, such that for "essential" functions, an alarm to the Caregiver is provided immediately if the PRC does not respond, or responds in the negative. On the other hand, if the activity is a routine, optional activity (bridge game) then monitor 312 (FIG. 1) does not generate an alarm unless more than a predetermined number (5 or 6) events are skipped, intentionally or inadvertently.

After collecting the data, the process proceeds to step S703, where the data on the number of "YES" responses, represented by the variable "X", is collected. The process then proceeds to step S705 where a predetermined threshold "Y", is retrieved from memory. Then in step S707, the monitor compares whether the number of "YES" responses is greater than the threshold (e.g., X>Y), and the process proceeds to step S711, if the response to the inquiry in step S707 is affirmative. On the other hand, if the response to the inquiry in step S707 is negative, the process proceeds to step S709 where an alert is generated, informing the Caregiver of the status of the PRC. For example, the status indication may indicate, event-specific inactivity (failure to participate in bridge games), or general inactivity status, such as failure to participate in a variety of different activities.

Figure 8:
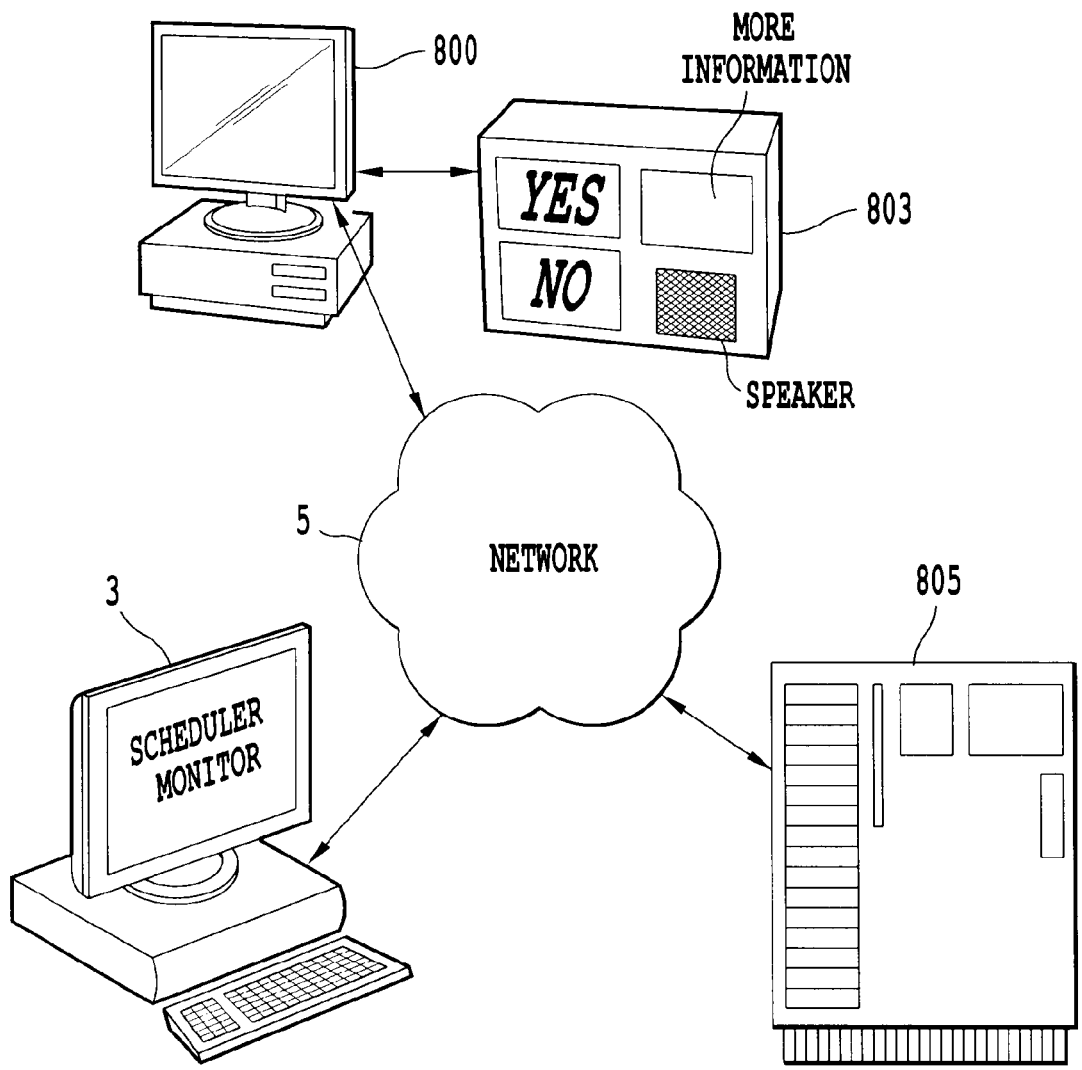
FIG. 8 is block diagram of a web-based embodiment of the present invention.

FIG. 8 is a block diagram of a web-based embodiment of the present invention. In this embodiment, the local interaction device includes a modified electronic photo frame 800 (which is a modified version of photo frame 1100 in FIG. 11), and a local interface device 803. The local interface device 803 may optionally include all of the features of local interaction device 1 (FIG. 3), although there is no need to include a display (unless a portable version is used) because the modified electronic photo frame 800 is used as the display. Schedule events and monitored activity is performed by the remote interface device 3, although the scheduling data and interaction data is set/collected in a web-server 805. The network 5 interconnects the devices.

In this embodiment, the modified electronic photo frame 800 operates as a conventional electronic photo frame, displaying photos downloaded from the web-server 805. However, when a scheduled event occurs, the modified electronic photo frame 800 displays a graphical (or video, or text) image of the invitation, and also conveys a signal to the local interface device 803 to produce an audio announcement. The PRC then interacts with the local interface device 803 to state his or her intentions. The interface data is then sent via the modified electronic photo frame 800 to the web-server 805 for processing.

Regarding the modifications to the photo frame 800, and peripheral interface (e.g., USB) that enables the local interface device 803 to communication with the processor used in the photo frame 800. The processor in the photo frame 800 is also programmed to convey message data between the web-server 805 to the local interface device 803. Furthermore the processor in the electronic photo frame 800 is configured to display text messages as well as photos. Also, the processor is configured to send messages either a predetermined times, or upon receipt of messages from the web-server 805 or the local interface device 803.

In this embodiment 805, the scheduling/monitoring software is hosted on the web-server 805. This allows the Caregiver to access the scheduling/monitor interface at any location.

As an alternative, the local interface device can be built into the photo-frame, such as, for example, a touchscreen, or as a separate touchscreen that cooperates with the photo-frame or monitor. More generally, the local interface can be a touchscreen interface that presents in a graphical format the "Yes", "No" and possibly "More Information" areas for selection by the PRC. When the touchscreen is not presenting an announcement of an event to the PRC, the touchscreen may present a graphics, or video image, advertising events that may be of interest to the PRC. As a further alternative, the local interface device (or photo-frame) includes a wireless (e.g., Infrared) remote control receiver that acknowledges a first key of a remote control (e.g., up key) as an affirmative response, and a second key on the remote control (e.g., down key) as a negative response. This way, the PRC need not get up from his or her chair or bed to respond to an invitation to participate in an event. Likewise, this wireless feature may be included in a watch, pendant, hearing aide, glasses or other wearable configuration.

The present invention may also be used in a networked environment. For example, a coordinator of an assisted care facility or independent living senior center may have a central remote interface device that connects via the network 5 to a plurality of local interaction devices 1. This way, the coordinator is provided with a centralized scheduling/monitoring device that is able to "fuse" information from the different local interaction devices to identify trends, and/or to provide a coordination service for monitoring/coordinating the activities of multiple PRCs. In this scenario the coordinator may use the networked devices to set multiple seatings for meals (e.g., adjust schedules for different subsets of people), thus providing an adaptive scheduling capability.

Figure 9:
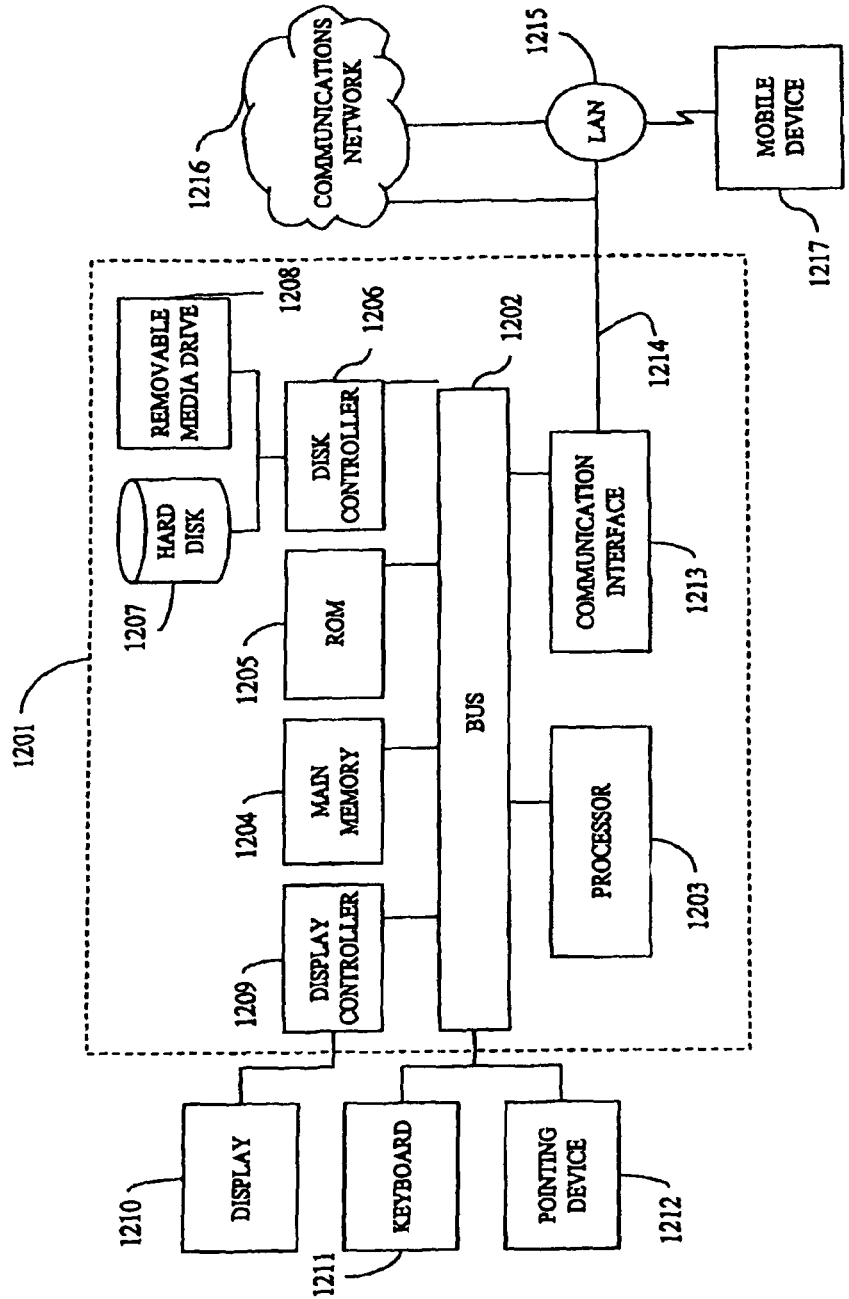
FIG. 9 is a block diagram of a computer that may be used to implement the processing and communication steps and operations of the present invention.
Figure 10:
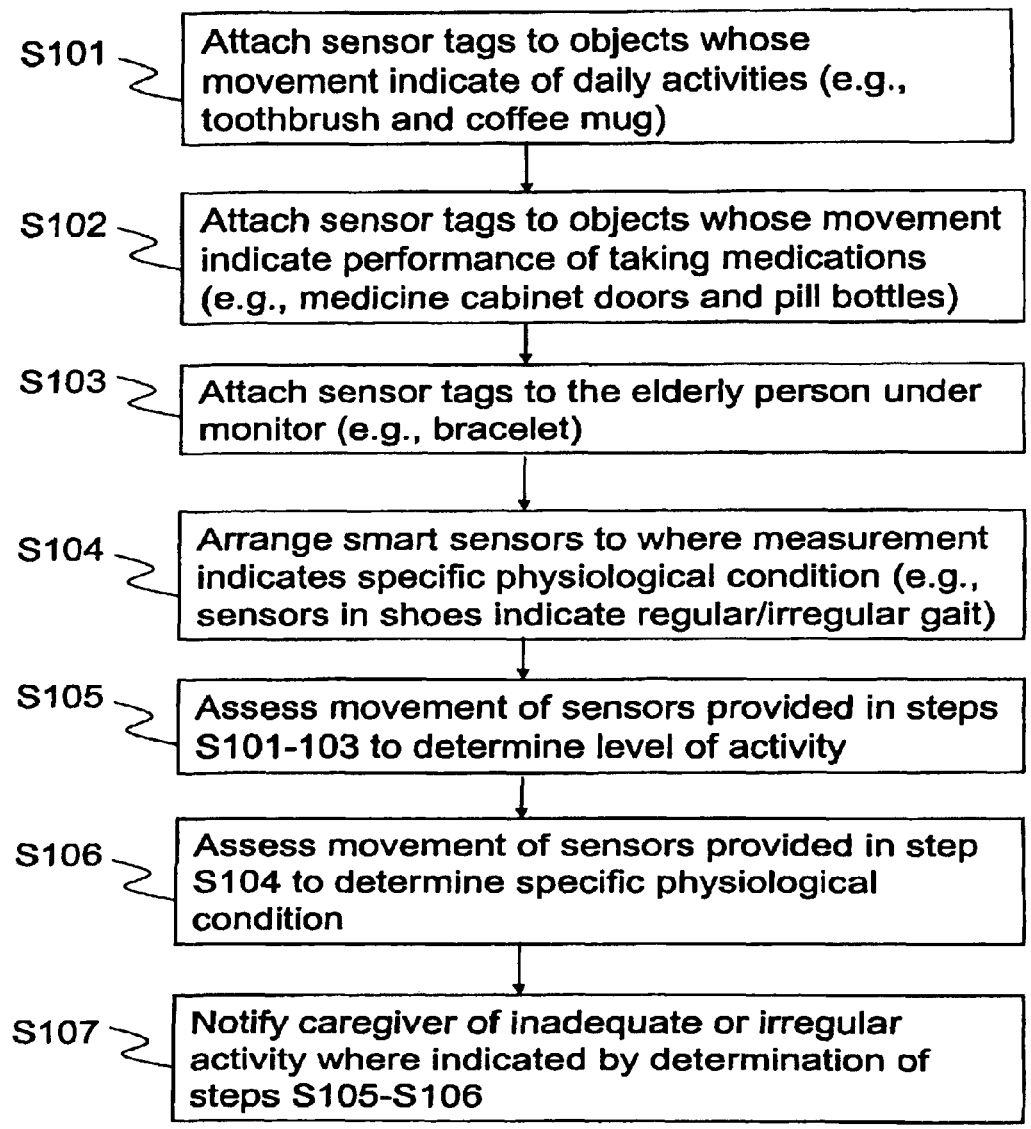
FIG. 10 is a flow diagram of a process for monitoring a subject according to the Background Art.

FIG. 9 illustrates a computer system 1201 upon which an embodiment of either the local interaction device 1 or remote interface 3 may be implemented. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

The invention may also be implemented by the preparation of application specific integrated circuits or by interconnecting an appropriate network of conventional component circuits, as will be readily apparent to those skilled in the art.

Obviously, numerous modifications and variations of the present invention are possible in light of the above teaching. It is therefore to be understood that within the scope of the appended claims, the invention may be practiced otherwise than as specifically described herein.

We claim:

1. A computer-based system for remotely coordinating activities for a plurality of persons under care, comprising:
    a remote computer that implements a centralized scheduling device that fuses information from a plurality of local interaction devices so as to coordinate activities for the plurality of persons under care;
    the plurality of local interaction devices that each including:
        an Input/Output device that exchanges messages and information with the remote computer to coordinate services for the plurality of persons under care;
        an event reminder mechanism configured to generate an announcement signal for a predetermined activity involving a third party that provides care for the plurality of persons under care; and
        an announcement mechanism that generates at least one of an audible announcement and a visual announcement regarding the activity;
    the remote computer further including a computer processor programmed to:
        receive an input signal regarding a beginning of the activity and automatically produce a notification if the activity is not initiated as planned;
        create a history of the activity planned for the person under care with the third party,
        provide a caregiver with remote access for producing customized activities involving the third party,
        monitor an actual activity of the person under care with the third party,
        receive input regarding a completion of the actual activity, and
        notify the centralized scheduling device of the completion of the actual activity,
    wherein the centralized scheduling device adjusts schedules for the plurality of persons under care to coordinate the activity performed by the third party, and
    each local interaction device being configured to await an indication via the Input/Output device that a particular person under care accepts delivery of an invitation for the activity, and is ready to take delivery of the activity, prior to delivery of the invitation.

2. The system of claim 1, wherein the third party being a therapist.

* * * * *